(12) United States Patent
Lin et al.

(10) Patent No.: US 10,828,635 B2
(45) Date of Patent: Nov. 10, 2020

(54) APPARATUS FOR ISOLATING BUBBLES

(71) Applicant: Tantti Laboratory Inc., Taoyuan (TW)

(72) Inventors: Pang Lin, Taoyuan (TW); Hui Chen, Taoyuan (TW)

(73) Assignee: Tantti Laboratory Inc., Taoyuan (TW)

( * ) Notice: Subject to any disclaimer, the term of this patent is extended or adjusted under 35 U.S.C. 154(b) by 210 days.

(21) Appl. No.: 16/239,672

(22) Filed: Jan. 4, 2019

(65) Prior Publication Data

US 2020/0215534 A1      Jul. 9, 2020

(51) Int. Cl.
| | | |
|---|---|---|
| *B01L 3/00* | (2006.01) | |
| *C12M 3/06* | (2006.01) | |
| *F16F 9/04* | (2006.01) | |
| *B03D 1/14* | (2006.01) | |

(52) U.S. Cl.
CPC ..... *B01L 3/5027* (2013.01); *B01L 2200/0684* (2013.01); *B03D 1/1462* (2013.01); *C12M 23/16* (2013.01); *F16F 9/0472* (2013.01)

(58) Field of Classification Search
CPC .......... B01L 3/5027; B01L 2200/0684; C12M 23/16; F16F 9/0472; B03D 1/1462; B01D 19/0042
See application file for complete search history.

(56) References Cited

U.S. PATENT DOCUMENTS 3,525,196 A      8/1970   Brieskorn

2005/0081716 A1      4/2005   Morita et al.
2007/0239097 A1*    10/2007   Nakayama .......... A61M 1/3627
                                                                      604/6.09
2008/0110344 A1      5/2008   Follette et al.

FOREIGN PATENT DOCUMENTS

TW      I524883      3/2016

OTHER PUBLICATIONS

Taiwan Search Report for Application No. 107136421, dated Mar. 22, 2019.
G. F. Christopher et al., "Microfluidic methods for generating continuous droplet streams", J. Phys. D: Appl. Phys. 40 (2007), R319-R336.

* cited by examiner

*Primary Examiner* — Jennifer Wecker
*Assistant Examiner* — Michael Paul Shimek
(74) *Attorney, Agent, or Firm* — Demian K. Jackson; Jackson IPG PLLC

(57) ABSTRACT

An apparatus for isolating bubbles from a liquid comprises at least a main body; an inlet tube and an outlet tube disposed at a side of the main body which includes an accommodation chamber and a column disposed atop, the inlet tube is formed with an aperture within the accommodation chamber, and the outlet tube is disposed at a position below the inlet tube; and a coupling tube disposed within the accommodation chamber, and includes a first end connected to the inlet tube and a second end corresponding to and separating from the outlet tube by a gap. During use, a liquid dispersed with bubbles is introduced through the inlet tube. The bubbles pass through the aperture along with a small portion of the liquid and ascend toward a top of the accommodation chamber and are then collected by the column.

10 Claims, 4 Drawing Sheets

APPARATUS FOR ISOLATING BUBBLES

FIELD OF THE INVENTION

The present invention relates to an apparatus for isolating bubbles from a liquid.

BACKGROUND OF THE INVENTION

"Tissue engineering" aims to restore, maintain and even enhance the functionality of tissues (organs). Many people suffer from organ failure every year. However, the donated organs are often in short supply, and the side effects after transplant surgery make organ donation and transplant unable to meet the medical needs. The current practice in tissue engineering, which is a cross-field emerging technology that combines life sciences and engineering, is to remove the target cells from the human body, culture in vitro until the cells grow to a sufficient amount, then transfer the cells into an artificial scaffold to form the tissue or organ of interest, and finally transplant the artificial tissue to the damaged part of the human body to repair and restore its original function. It has brought a new vision for the treatment of organ failure.

In order to provide an environment that allows cells to grow and differentiate smoothly during tissue engineering, a tissue scaffold must be used, in which cells may migrate and grow. The tissue scaffold itself may contain cells, growth factors, extracellular matrix components, for cell growth, tissue differentiation and remodeling in vitro or in vivo, which ultimately can produce tissues for experimental or further transplantation applications. The scaffold is to provide a three-dimensional framework suitable for cell growth and, thus, is generally called a three-dimensional scaffold. It includes a large number of micropore structures stacked together and integrally forms a specific architecture provided for cell attachment or inoculation, whereby the cells are guided to grow and differentiate along the designed three-dimensional directions, producing a regenerated tissue or organ. Conventional scaffold preparation techniques include salting-out processes, freeze drying processes, and solid freeform fabrication processes.

At present, researcher have developed a microfluidic method for fabricating a three-dimensional scaffold, which is practiced by passing a liquid and a gas through a flow-focusing microfluidizer, similar to a bubble blowing process. The bubbles dispersed in the liquid are then packed into a three-dimensional scaffold. This fabrication method is not only low in cost but also has the advantage of rapid production. In addition, since this method utilizes a steady air flow rate to blow and fabricate bubbles through the flow-focusing microfluidizer, the generated bubbles are uniform in size, and the tissue scaffold thus produced has a uniform porosity and a highly controlled density.

The above-mentioned microfluidic method produces bubbles that are dispersed in a liquid, and a proportion of the bubbles is low. At this time, the bubbles must be isolated from the liquid, collected, and packed into a three-dimensional scaffold. However, since a large number of bubbles are collected and stacked to form a so-called foam, its rheological behavior exhibits a hysteresis, wherein a flow viscosity of the foam increases rapidly as the bubble content increases (and a relative content of the liquid decreases). When the external pressure changes greatly, the foam can be easily destroyed, and the density and mass of individual small bubbles are almost zero, which is easily driven by the liquid turbulence and is difficult to control. All of the above factors make the process of processing bubbles much different from processing general fluids, and new technology is urgently needed to solve them.

SUMMARY OF THE INVENTION

In a primary aspect of the invention provided herein is an apparatus for isolating bubbles from a liquid.

The apparatus for isolating bubbles comprises a main body including an accommodation chamber and a column disposed atop and in fluid communication with the accommodation chamber; an inlet tube disposed at a side of the main body, the inlet tube is formed with an aperture within the accommodation chamber; an outlet tube disposed at a side of the main body and at a position below the inlet tube; and a coupling tube disposed within the accommodation chamber and having a first end connected to the inlet tube and a second end corresponding to and separating from the outlet tube by a gap.

According to the present invention, a liquid dispersed with bubbles is introduced through the inlet tube. The bubbles pass through the aperture along with a small portion of the liquid and ascend toward a top of the accommodation chamber and are then collected by the column. A remaining large portion of the liquid continues to flow toward the coupling tube from the inlet tube and is discharged outside the main body via the outlet tube. The small portion of the liquid passing through the aperture enters the outlet tube via the gap, where it rejoins the remaining portion of the liquid and flows out of the main body, thereby isolating the bubbles from the liquid.

BRIEF DESCRIPTION OF THE DRAWINGS

The invention will become more readily apparent to those ordinarily skilled in the art after reviewing the following detailed description and accompanying drawings, in which.

DETAILED DESCRIPTION OF PREFERRED EMBODIMENTS

Hereinafter, the invention will be described in detail with drawings illustrating various embodiments of the present invention. However, the concept of the present invention may be embodied in many different forms and should not be construed as limitative of the exemplary embodiments set forth herein.

Figure 1:
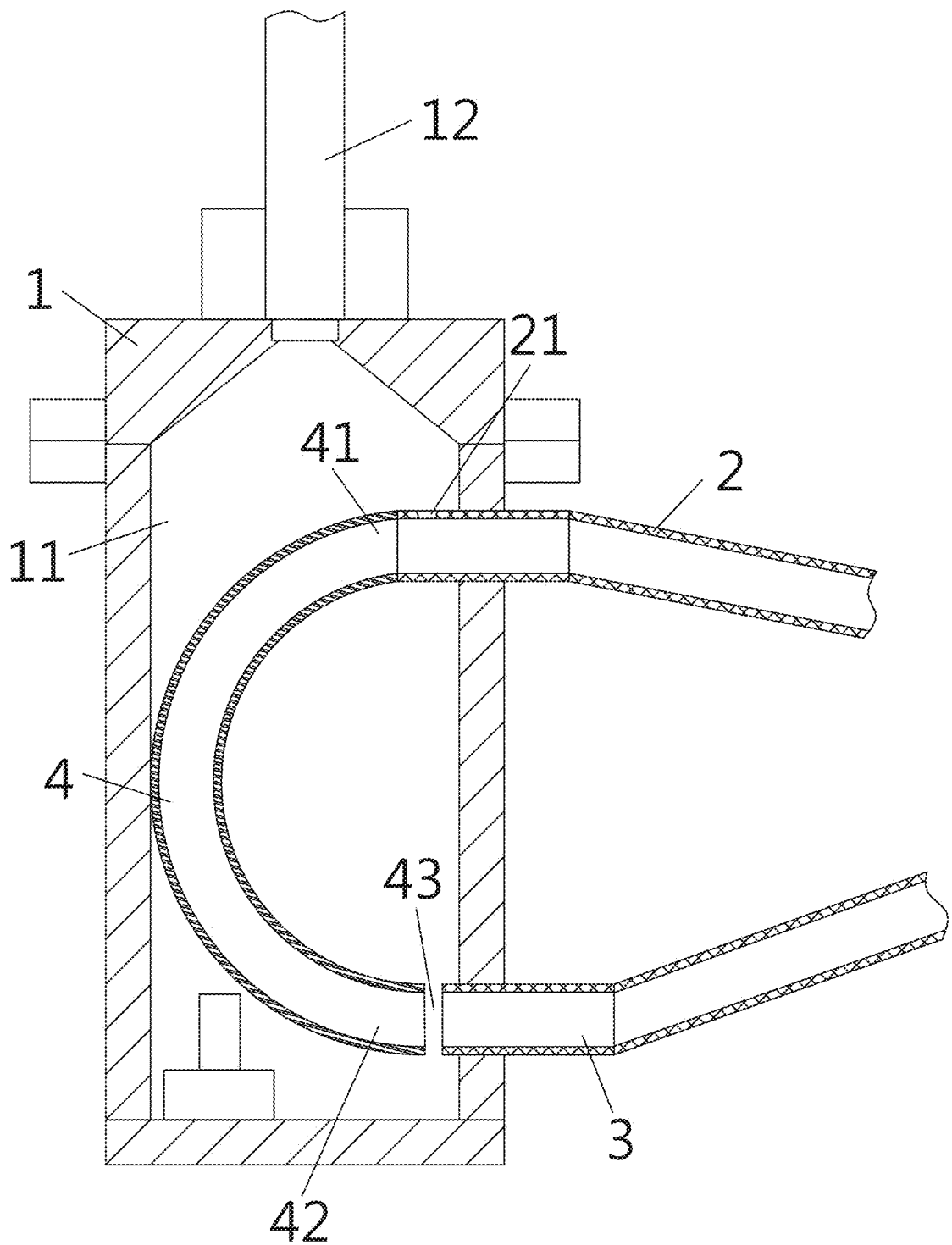
FIG. 1 is a schematic structural view of an apparatus for isolating bubbles according to the invention.

Referring to FIG. 1, an apparatus for isolating bubbles according to the invention comprises: a main body 1, an inlet tube 2, an outlet tube 3, and a coupling tube 4.

The main body 1 is a rigid structure, including an accommodation chamber 11 and a column 12 disposed atop and in fluid communication with the accommodation chamber 11. The column 12 extends upward from a top of the accommodation chamber 11.

The inlet tube 2 is disposed at a side of the main body 1. The inlet tube 2 is formed with an aperture 21 within the accommodation chamber 11, and the aperture 21 is located at an upper position of the inlet tube 2.

The outlet tube 3 is disposed at a side of the main body 1 and at a position below the inlet tube 2.

The coupling tube 4 is disposed within the accommodation chamber 11, which includes a first end 41 connected to the inlet tube 2 and a second end 42 corresponding to and separating from the outlet tube 3 by a gap 43. The first end 41 of the coupling tube 4 is positioned higher than the second end 42 of the coupling tube 4.

Figure 2:
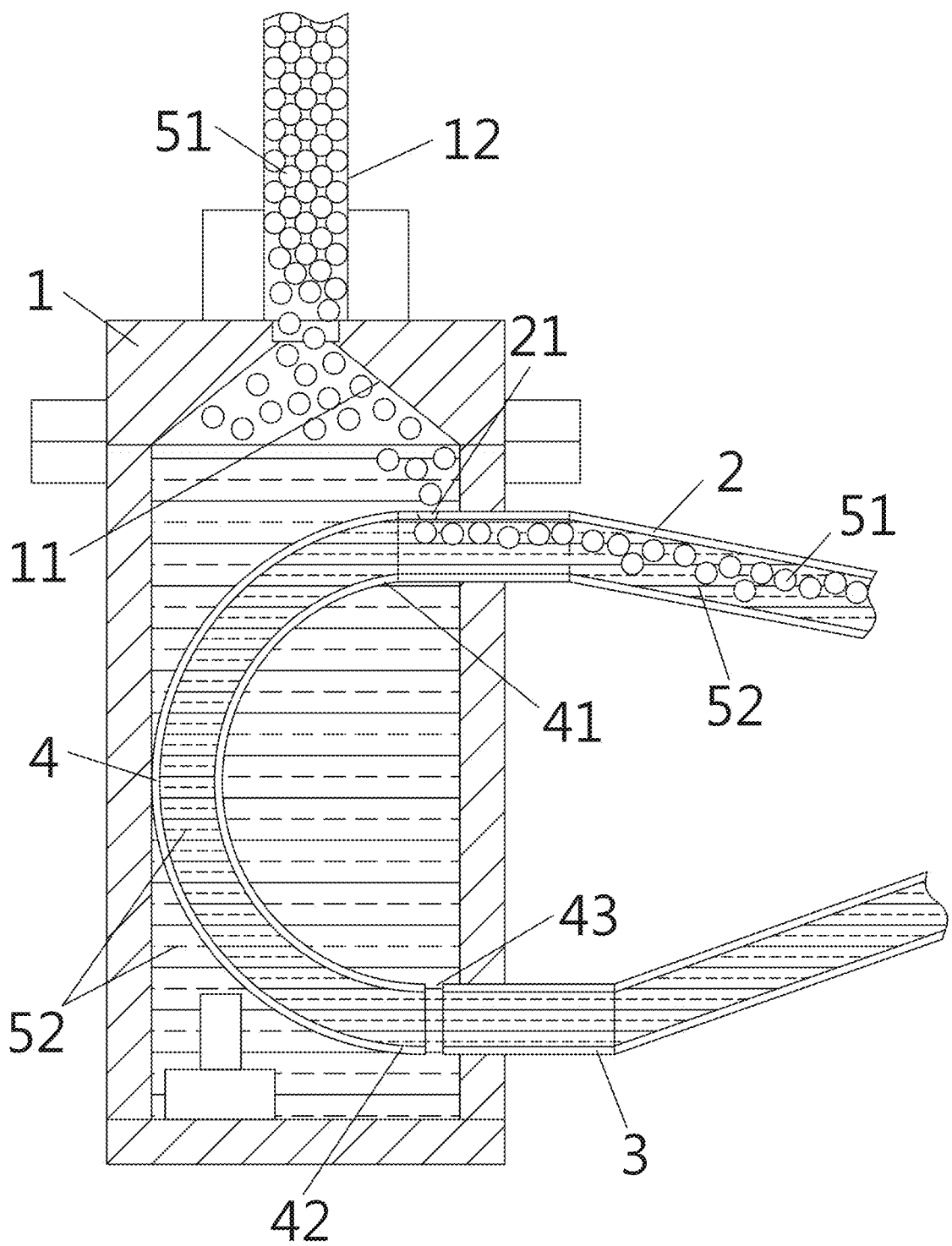
FIG. 2 is a schematic view showing the apparatus for isolating bubbles according to the invention during use.
Figure 3:
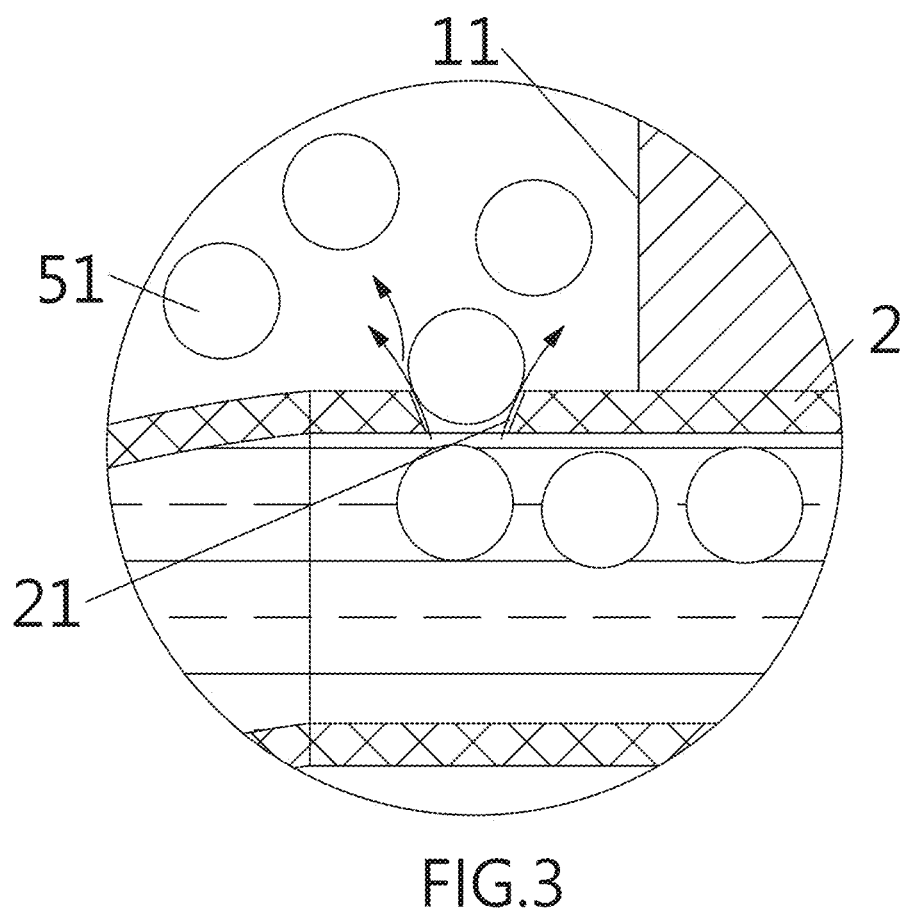
FIG. 3 is an enlarged view showing the apparatus for isolating bubbles according to the invention during use.

Referring to FIG. 2 and FIG. 3 for the usage, a liquid 52 dispersed with bubbles 51 is introduced through the inlet tube 2. The bubbles 51 spurt through the aperture 21 along with a small portion of the liquid 52 and ascend toward the top of the accommodation chamber 11 and are then collected by the column 12. The pressure difference between the inside and the outside of the inlet tube 2 is the source of power for the small portion of the liquid 52 to spurt from the aperture 21. A remaining large portion of the liquid 52 enters the outlet tube 3 after passing through the first end 41 of the coupling tube 4 and the second end 42 of the coupling tube 4 and flows out of the main body 1. The small portion of the liquid 52 spurting through the aperture 21 enters the outlet tube 3 via the gap 43, where it rejoins the remaining portion of the liquid 52 that flows in from the inlet tube 2, and all the liquid 52 flows out of the main body 1. Therefore, a volume of the liquid 52 in the main body 1 does not continue to accumulate and endlessly increase. In a steady operation state, the volume of the liquid 52 in the main body 1 is almost constant. In the above process, the large portion of the liquid 52 carried by the inlet tube 2 flows directly downward to the outlet tube 3 via the coupling tube 4, thereby avoiding a serious interference effect on the collection of the bubbles 51 occurring above.

After collection, the bubbles described herein can be used in many technical fields, such as chemical and biochemical analysis. As the bubbles form in a spherical configuration spontaneously during the process of collecting bubbles, they undergo self-assembling into a close-packed arrangement. The solution contained in the interface between the adjacent bubbles may be gelatinized by a chemical reaction, so that the relative positions of the adjacent bubbles is fixed to form an elastic three-dimensional scaffold. The interface between the adjacent bubbles may be broken into a small hole through a low-pressure expansion process, so that the adjacent bubbles are merged into a continuous space. The bubble assembly has a sponge-like or honeycomb-like structure, and the interior thereof includes a large number of spherical pores communicating one another which allow cells to be inoculated and attach.

The above-mentioned three-dimensional scaffold has special physical properties, such as light weight, low thermal conductivity, high porosity and so on, and thus is often applied in various engineering and medical fields, and the most noticeable one is used as a tissue scaffold for culturing cells. It functions to imitate the extracellular matrix so that the cells can grow in the scaffold by attaching or perfusing or inoculating the selected cells onto the scaffold. Alternatively, the three-dimensional scaffold itself may act as a culture medium, allowing the cells to grow therein. Afterwards, the cells are given appropriate growth signals and chemical stimuli, so that the cells proliferate, grow and differentiate in a simulated environment, and then form as a regenerated tissue or organ for a therapeutic target. After transplanting into a patient's body, the regenerated counterpart can replace the original damaged, or dysfunctional or necrotic tissue or organ. The most commonly used natural materials for tissue scaffolds are collagen-like materials obtained from animal sources and plant-derived hydrogrels, such as gelatin, collagen, chitosan or sodium alginates. Suitable artificial materials comprise polylactates (PLLA), polyglycolates (PGA), poly-lactic-co-glycolic acid (PLGA), and the like. In addition to supplying the growth environment for cells, the tissue scaffold can also regulate the connection among cells and prevent cells from compressing one another, so as to ensure that the growth of the cells are supported by the best environment.

Figure 4:
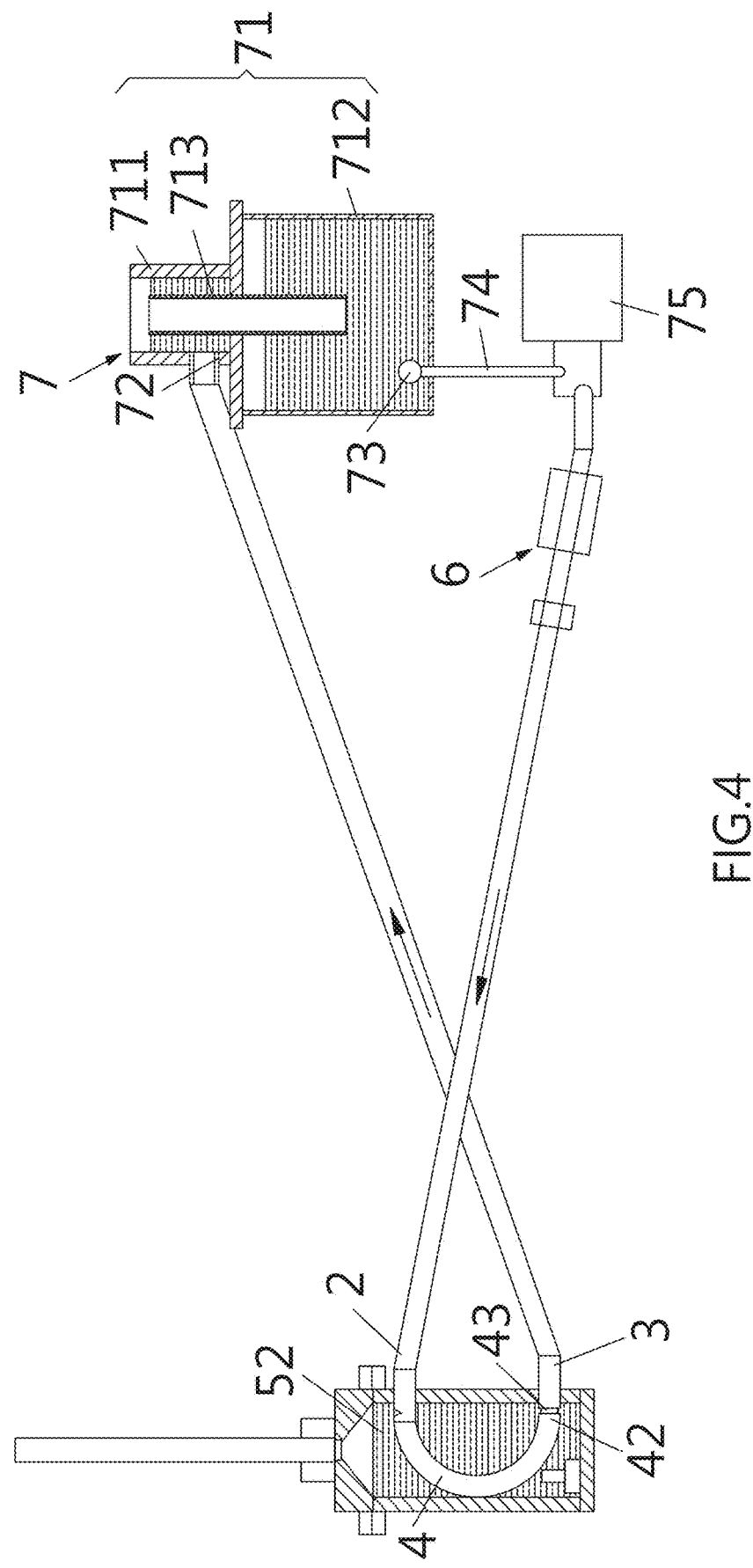
FIG. 4 is another schematic structural view of the apparatus for isolating bubbles according to the invention.

Furthermore, the invention can further be provided with a bubble generating device 6 and a liquid recovery device 7. As shown in FIG. 4, the bubble generating device 6 is connected to the inlet tube 2 to provide the liquid 52 dispersed with the bubbles 51. The liquid recovery device 7 is connected to the outlet tube 3 for receiving the liquid 52 separated from the bubbles 51. The liquid recovery device 7 includes a recovery tank 71 for accommodating the liquid 52. The recovery tank 71 is provided with an inlet port 72 and an outlet port 73, and the inlet port 72 is positioned higher than the outlet port 73 and also higher than the second end 42 of the coupling tube 4. The inlet port 72 is connected to the outlet tube 3, and the outlet port 73 is connected to a conveying member 75 (such as a pump) via an outlet pipe 74. The conveying member 75 is connected to the outlet pipe 74 to move the liquid 52 to continuously flow through the bubble generating device 6, the inlet tube 2, the coupling tube 4 and the outlet tube 3 and return to the recovery tank 71.

In the embodiment shown in FIG. 4, the recovery tank 71 includes a first tank 711 and a second tank 712 disposed beneath the first tank 711, and a tube 713 coupled between the first tank 711 and second tank 712. The inlet port 72 is disposed at the first tank 711, and the outlet port 73 is disposed in the second tank 712. The tube 713 is vertically disposed between the first and second tanks 711 and 712. The tube 713 has a top end located at a position lower than a top end of the first tank 711. The liquid 52 flows from the outlet tube 3 through the inlet port 72 into the first tank 711. When the level of the liquid 52 is higher than the top end of the tube 713, the liquid 52 enters the tube 713 from the top end of the tube 713 and then flow into the second tank 712, and finally flow out from the outlet port 73.

The bubble generating device and the method for generating bubbles dispersed in the liquid are generally described in co-pending U.S. patent application Ser. No. 15/713,822 assigned to the Applicant, entitled "Method and Apparatus of Generating Substantially Monodisperse Droplets," the entire disclosure of which is incorporated herein for reference.

When the embodiment of FIG. 4 is in use, the liquid 52 is introduced into the first tank 711 with a liquid level higher than the top end of the tube 713. The liquid 52 flows from the tube 713 into the second tank 712, and is introduced into the bubble generating device 6 from the outlet port 73 through the outlet pipe 74 by using the conveying member 75. The bubbles 51 generated by the bubble generating device 6 are dispersed in the liquid 52 being transported in the inlet tube 2. Referring to FIG. 2, when the liquid 52 is transported in the inlet tube 2, the bubbles 51 will slowly move to an upper position of the inlet tube 2 due to their lower density. When the liquid 52 dispersed with the bubbles 51 flows through the aperture 21, the bubbles 51 located at the upper position of the inlet tube 2 spurt from the aperture 21 along with a small portion of the liquid 52, and ascend toward the top of the accommodation chamber 11. When more and more of the bubbles 51 are spurted from the aperture 21, the upper bubbles 51, pushed by the lower bubbles 51 due to buoyancy, move toward the interior of the column 12. The bubbles 51 moving into the column 12 self-assemble into a closest packed arrangement during the upward movement, thereby completing the isolation and collection of the bubbles 51.

The major portion of the liquid 52 contained in the inlet tube 2 enters the outlet tube 3 via the coupling tube 4 and flows out of the main body 1. The minor portion of the liquid 52 spurted from the aperture 21 can also enter the outlet tube 3 through the gap 43 and flow out of the main body 1. Therefore, the liquid 52 in the outlet tube 3 flows into the first tank 711 of the recovery tank 71 through the inlet port 72, thereby recycling the liquid 52.

The invention provides a preferred and feasible apparatus for isolating bubbles accordingly. While the invention has been described with reference to the preferred embodiments above, it should be recognized that the preferred embodiments are given for the purpose of illustration only and are not intended to limit the scope of the present invention and that various modifications and changes, which will be apparent to those skilled in the relevant art, may be made without departing from the spirit and scope of the invention.

What is claimed is:

1. An apparatus for isolating bubbles, comprising:
   a main body including an accommodation chamber and a column disposed atop and in fluid communication with the accommodation chamber;
   an inlet tube disposed at a side of the main body, the inlet tube being formed with an aperture within the accommodation chamber;
   an outlet tube disposed at a side of the main body and at a position below the inlet tube; and
   a coupling tube disposed within the accommodation chamber, the coupling tube comprises a first end connected to the inlet tube and a second end corresponding to and separating from the outlet tube by a gap;
   wherein a liquid dispersed with bubbles is introduced through the inlet tube, the bubbles pass through the aperture along with a small portion of the liquid and ascend toward a top of the accommodation chamber and are then collected by the column, and a remaining large portion of the liquid continues to flow toward the coupling tube from the inlet tube and is discharged outside the main body via the outlet tube, and the small portion of the liquid passing through the aperture enters the outlet tube via the gap, where it rejoins the remaining portion of the liquid and flows out of the main body.

2. The apparatus as claimed in claim 1, further comprising a bubble generating device connected to the inlet tube to provide the liquid dispersed with the bubbles.

3. The apparatus as claimed in claim 2, further comprising a liquid recovery device connected to the outlet tube for receiving the liquid.

4. The apparatus as claimed in claim 3, wherein the liquid recovery device comprises a recovery tank for accommodating the liquid, the recovery tank being provided with an inlet port and an outlet port, the inlet port being connected to the outlet tube, and the outlet port being connected to the bubble generating device via an outlet pipe.

5. The apparatus as claimed in claim 4, wherein the inlet port is positioned higher than the outlet port.

6. The apparatus as claimed in claim 4, wherein the inlet port is positioned higher than the second end of the coupling tube.

7. The apparatus as claimed in claim 4, wherein the liquid recovery device further comprises a conveying member connected to the outlet pipe.

8. The apparatus as claimed in claim 1, wherein the first end of the coupling tube is positioned higher than the second end of the coupling tube.

9. The apparatus as claimed in claim 1, wherein the column extends upward from the top of the accommodation chamber.

10. The apparatus as claimed in claim 1, wherein the aperture is located at an upper position of the inlet tube.

* * * * *